United States Patent [19]

Furlenmeier

[11] Patent Number: 4,716,227
[45] Date of Patent: Dec. 29, 1987

[54] PROCESS FOR MANUFACTURING CEPHALOSPORIN ESTERS

[75] Inventor: André Furlenmeier, Basle, Switzerland

[73] Assignee: Hoffmann-La Roche Inc., Nutley, N.J.

[21] Appl. No.: 795,948

[22] Filed: Nov. 7, 1985

[30] Foreign Application Priority Data

Nov. 15, 1984 [CH] Switzerland ............... 5470/84

[51] Int. Cl.[4] ............... C07D 501/18; A61K 31/545
[52] U.S. Cl. ........................... 540/230; 514/209; 514/228
[58] Field of Search ................ 514/209; 540/230

[56] References Cited

U.S. PATENT DOCUMENTS 4,405,782 9/1983 Palomo-Coll et al. ............... 544/21

OTHER PUBLICATIONS

Oediger et al., Synthesis, Nov. 1982, pp. 591–598.

Primary Examiner—Nicholas S. Rizzo
Attorney, Agent, or Firm—Jon S. Saxe; Bernard S. Leon; George W. Johnston

[57] ABSTRACT

Cephalosporin esters of the formula

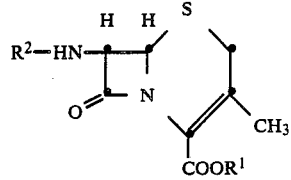

wherein $R^2$ is hydrogen or acyl and $R^1$ is a group which is readily removable by hydrolysis, and pharmaceutically acceptable acid addition salts of basic compounds of formula I in which $R^2$ is an acyl group, may be prepared by reacting 7-amino-3-methyl-3-cephem-4-carboxylic acid (7-ADCA) in a partially chlorinated lower alkane with a bicyclic amidine of the formula

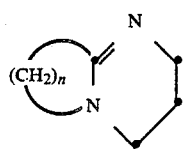

wherein n is the integer 3, 4 or 5, and a halide of the formula $X-R^1$   III wherein X is halogen and $R^1$ has the above significance, if desired, treating the resulting compound of formula I in which $R^2$ is hydrogen with an unprotected or optionally protected acylating agent, cleaving off a protecting group which may be present and, if desired, treating a resulting basic compound of formula I in which $R^2$ is an acyl group into a pharmaceutically acceptable acid addition salt.

15 Claims, No Drawings

PROCESS FOR MANUFACTURING CEPHALOSPORIN ESTERS

BACKGROUND OF THE INVENTION

This invention relates to cephalosporins.

SUMMARY OF THE INVENTION

The present invention describes a process for producing cephalosporin esters of the formula

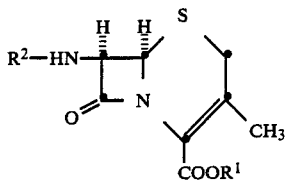

wherein $R^2$ is hydrogen or acyl and $R^1$ is a group which is readily removable by hydrolysis,
and of pharmaceutically acceptable acid addition salts of basic compounds of formula I in which $R^2$ is acyl, which process comprises reacting 7-amino-3-methyl-3-cephem-4-carboxylic acid (7-ADCA) in a partially chlorinated lower alkane with a bicyclic amidine of the formula

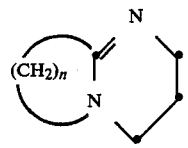

wherein n is the integer 3, 4 or 5, and a halide of the formula

     III wherein X is halogen and $R^1$ has the above significance,
so as to form compound I wherein $R^2$ is hydrogen; if desired, treating the resulting compound of formula I in which $R^2$ is hydrogen with an unprotected or an optionally protected acylating agent, cleaving off a protecting group which may be present thereby to form compound I wherein $R^2$ is acyl; and, if desired, treating a resulting basic compound of formula I in which $R^2$ is acyl so as to form a pharmaceutically acceptable acid addition salt.

The cephalosporin esters of formula I wherein $R^2$ is acyl are valuable medicaments for the control or prophylaxis of infectious diseases, especially by the oral route. They have antibiotic, especially antibacterial, activity and a broad spectrum of activity against gram-positive and gram-negative bacteria.

DETAILED DESCRIPTION OF THE INVENTION

This invention is concerned with a process for producing a cephalosporin ester of the formula

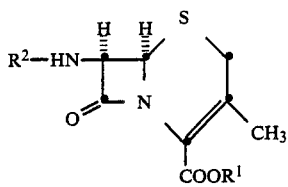

wherein $R^2$ is hydrogen or acyl and $R^1$ is a group which is readily removable by hydrolysis,
and of pharmaceutically acceptable acid addition salts of basic compounds of formula I in which $R^2$ is acyl, which process comprises reacting 7-amino-3-methyl-3-cephem-4-carboxylic acid (7-ADCA) in a partially chlorinated lower alkane with a bicyclic amidine of the formula

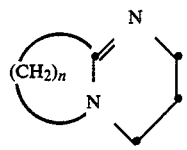

wherein n is the integer 3, 4 or 5, and a halide of the formula

     III wherein x is halogen and $R^1$ has the above significance, thereby forming compounds of formula I wherein $R^2$ is hydrogen.

If desired, one can treat the resulting compound of formula I in which $R^2$ is hydrogen with an unprotected or optionally protected acylating agent and cleave off a protecting group which may be present thereby forming compound I wherein $R^2$ is acyl. If desired, one can treat a resulting basic compound of formula I in which $R^2$ is acyl so as to form a pharmaceutically acceptable acid addition salt thereof.

For the manufacture of compounds of formula I in which $R^2$ is acyl, an ester of the formula

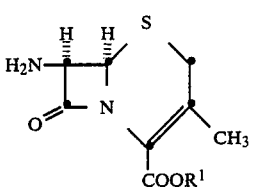

wherein $R^1$ has the above significance (i.e., compound I wherein $R^1$ is hydrogen),
which is obtained after the treatment of 7-ADCA with compounds II and III, is preferably not isolated, but is converted directly by acylation in a so-called "one-pot process" into the desired compound of the formula

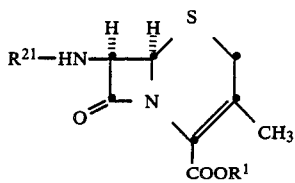

Ib wherein $R^1$ has the above significance and $R^{21}$ is an acyl (i.e., compound I wherein $R^2$ is acyl).

The term "acyl" or "acyl group" used in the present description preferably denotes any conventional acyl group derived from carboxylic acids, especially acyl groups which are conventionally usable in cephalosporin chemistry for the 7-amino group. The following groups can be mentioned as examples thereof: Q—(A)$_p$—CO— and Q—C(=NOR$^3$)CO— in which A is lower alkylene, Q is aryl, heteroaryl or 5- to 7-membered cycloalkyl, cycloalkenyl, heterocycloalkyl or heterocycloalkenyl, $R^3$ is lower alkyl, lower alkenyl or the group —CH$_2$COOR$^4$ or —C(CH$_3$)$_2$COOR$^4$, the group —COOR$^4$, carboxy or a readily hydrolyzable ester group and p is the integer 0 or 1, whereby these groups can be unsubstituted or substituted in one or more positions, for example, by amino, hydroxy, lower alkyl, lower alkoxy or halogen. Examples of such groups are: phenylacetyl, 2-amino-2-phenylacetyl, 2-amino-2-(4-hydroxyphenyl)acetyl, 2-amino-2-(1,4-cyclo-hexadien-1-yl)acetyl, 2-(2-amino-4-thiazolyl)acetyl, 2-(2-furyl)-2-methoxyiminoacetyl, 2-(2-amino-4-thiazolyl)-2-methoxyimino-acetyl, 2-(2-amino-4-thiazolyl)-2-carboxy-methoxyimino-acetyl and 2-(2-amino-4-thiazolyl)-2-pivaloyloxymethoxycarbonylmethoxyimino-acetyl.

The term "group which is readily removable by hydrolysis" preferably denotes any conventional groups which are hydrolyzable or cleavable under physiological conditions. Especially suitable are lower alkanoyloxy-lower alkyl groups such as the acetoxymethyl, pivaloyloxymethyl, 1-acetoxyethyl and 1-pivaloyloxyethyl groups and lower alkoxycarbonyl-lower alkyl groups such as the methoxycarbonyloxymethyl, 1-ethoxycarbonyloxyethyl and 1-isopropoxycarbonyloxyethyl group. The term "lower" denotes residues and compounds of 1 to 7, preferably a maximum of 4, carbon atoms. The term "alkyl" and terms derived therefrom such as alkoxy, alkylene, alkanoyl and alkenyl denote not only straight-chain but also branched hydrocarbon groups (e.g., methyl, ethyl, isopropyl, t-butyl and 2-butyl) and the corresponding groups derived therefrom.

The term "aryl" preferably denotes a phenyl group which can be unsubstituted or substituted in one or more positions with, for example, amino, hydroxy, lower alkyl, lower alkoxy or halogen. The term "heteroaryl" preferably denotes a 5- or 6-membered heteroaromatic group with at least one oxygen, sulphur or nitrogen atom which can be unsubstituted or substituted in one or more positions with, for example, amino, hydroxy, lower alkyl, lower alkoxy or halogen. Preferred is 2-amino-4-thiazolyl. The term "halogen" includes all four halogens, fluorine, chlorine, bromine and iodine.

In carrying out the process in accordance with the invention the 7-ADCA can be suspended in a partially chlorinated lower alkane, preferably in methylene chloride or chloroform, whereupon the suspension is treated with the bicyclic amidine of formula II, preferably 1,8-diazobiclo[5.4.0]undec-7-ene (DBU), as the salt-former. The salt-former should be used in stoichiometric amounts or, as is preferred, in a slight deficiency, as the addition of an excess may lead to undesired Δ$^2$-isomerization in the cephalosporin skeleton.

The sale of formula II which is formed is subjected to the esterification in accordance with the invention by adding a halide of formula III, especially an iodide, e.g. pivaloyloxymethyl iodide. To avoid an undesired yellow colouration, the reaction is preferably carried out with the exclusion of light.

For the manufacture of the products of formula Ib, the thus-obtained ester of formula Ia can be acylated. Any conventional agents which yield the acyl residue $R^{21}$ can be used as the acylating agent. Although not essential, amino groups which may be present in the acylating agent generally are protected; and aliphatic amino groups (e.g. when $R^{21}$ is 2-amino-2-phenylacetyl, 2-amino-2-(4-hydroxyphenyl)acetyl, 2-amino-2-(1,4-cyclohexadien-1-yl)acetyl) can be protected, for example, by trityl or by a group of the formula $R^5R^6C=CR^7$— in which $R^5$ is lower alkanoyl, lower alkoxycarbonyl or benzoyl; $R^6$ is hydrogen; lower alkyl, lower alkanoyl, lower alkoxycarbonyl or cyano and $R^7$ is hydrogen or lower alkyl (e.g. 1-methyl-2-methoxycarbonylvinyl, 1-methyl-2-benzoylvinyl, 2,2-(di-ethoxycarbonyl)vinyl and 1-methyl-1-benzoylvinyl) and aromatic amino groups (e.g. when $R^{21}$ is 2-(2-amino-4-thiazolyl)acetyl or 2-(2-amino-4-thiazolyl)-2-methoxyimino-acetyl) are preferably protected by groups which are cleavable by acidic hydrolysis (e.g. the t-butoxy-carbonyl or trityl groups), groups which are cleavable by basic hydrolysis (e.g. the trifluoroacetyl group), or by a chloroacetyl, bromoacetyl or iodoacetyl group which can be cleaved off with thiourea.

The corresponding acid can be used as the acylating agent, and in this case the condensation is carried out in the presence of a condensation agent, for example a carbodiimide such as dicyclohexylcarbodiimide. Corresponding acid halides can also be used. However, there are preferably used thioesters of the corresponding acids, especially the 2-benzthiazolyl thioesters. This has the advantage that aromatic amino groups (e.g. when $R^{21}$ signifies 2-(2-amino-4-thiazolyl)acetyl or 2-(2-amino-4-thiazolyl)-2-methoxyimino-acetyl) need not be protected. 2-(2-Amino-4-thiazolyl)-2-(Z)-methoxyimino-acetic acid 2-benzthiazolyl thioester is a preferred 2-benzthiazolyl thioester.

After the acylation of compound Ia, amino protecting groups which may be present are removed. Protecting groups which are cleavable by acidic hydrolysis are preferably removed with formic acid or trifluoroacetic acid. Protecting groups which are cleavable by basic hydrolysis are preferably removed with aqueous alkali metal hydroxide solution. The chloroacetyl, bromoacetyl or iodoacetyl group is preferably removed with thiourea. The group of the formula $R^5R^6C=CR^7$— is removed, for example, by treatment with water (optionally in admixture with a water-miscible solvent such as acetone, tetrahydrofuran, dioxan or the like) and an acid such as hydrochloric acid, sulphuric acid, p-toluenesulphonic acid or a sulphonated ion exchanger.

As mentioned above, the entire process is preferably carried out in a so-called "one-pot process", i.e. without isolating the intermediates obtained.

The reaction temperature lies in each step of the process preferably in the range of about 0° to about 40° C., whereby the "one-pot process" reaction is preferably carried out at room temperature (about 20° to about 25° C.).

The inventive process provides significant advantages with respect to production technology because it can be carried out smoothly in the same solvent and in good yield. It is especially suitable for the manufacture of 7-[2-(2-amino-4-thiazolyl)-2-(Z)-methoxyiminoacetamido]-3-methyl-3-cephem-4-carboxylic acid pivaloyloxymethyl ester, in which case DBU is preferably used as the salt-former, methylene chloride or chloroform is preferably used as the solvent, pivaloyloxymethyl iodide is preferably used as the halide of formula III and 2-(2-amino-4-thiazolyl)-2-(Z)-methoxyimino-acetic acid 2-benzthiazolyl thioester is preferably used as the acylating agent and the reaction is preferably carried out in a "one-pot process", whereby the additional step of cleaving off the amino protecting groups does not apply.

Basic compounds of formula Ib (i.e. compounds of formula Ib which have a basic acyl group) can be converted, if desired, into any conventional pharmaceutically acceptable acid addition salts, whereby their manufacture can be carried out according to methods which are known per se and which are familiar to any person skilled in the art. There come into consideration not only salts with inorganic acids, but also salts with organic acids, for example hydrochlorides, hydrobromides, sulphates, nitrates, citrates, acetates, maleates, succinates, methanesulphonates, p-toluenesulphonates and the like. In a particular embodiment of the present invention is concerned with the manufacture of the hydrochloride of 7-[2-(2-amino-4-thiazolyl)-2-(Z)-methoxyimino-acetamido]-3-methyl-3-cephem-4-carboxylic acid pivaloyloxymethyl ester.

The cephalosporin esters of formula Ib and the pharmaceutically acceptable acid addition salts of basic compounds of formula Ib are valuable medicaments for the control or prophylaxis of infectious diseases, especially by the oral route. They have antibiotic, especially antibacterial, activity and a broad spectrum of activity against gram-positive and gram-negative bacteria.

The following Example illustrates the present invention in more detail. Temperatures are in degree Celsius, and room temperature is about 20° C. to about 25° C. The Example was carried out as written.

EXAMPLE 19.2 g (90 mmol) of 7-ADCA are suspended in 500 ml of methylene chloride, treated with 13.2 ml (84 mmol) of DBU and stirred at room temperature for 30 minutes. 16 ml (100 mmol) of pivaloyloxymethyl iodide are subsequently added. The mixture is stirred at room temperature for 30 minutes, treated with 28 g (80 mmol) of 2-(2-amino-4-thiazolyl)-2-(Z)-methoxyimino-acetic acid 2-benzthiazolyl thioester and stirred at room temperature for 3.5 hours with the exclusion of light. The turbid solution obtained is filtered, washed three times with 1 l of water each time and evaporated at 30° C. in vacuo. The yellow residue is dissolved in 720 ml of isopropanol and 12 ml of 25 percent hydrochloric acid. Crystallization occurs after a short time. 860 ml of hexane are then introduced within 30 minutes while stirring. The crude hydrochloride which crystallizes out is filtered off under suction, dried in vacuo and recrystallized from ethanol/hexane. There are obtained 30.8 g (70%) of 7-[2-(2-amino-4-thiazolyl)-2-(Z)-methoxyimino-acetamido]-3-methyl-3-cephem-4-carboxylic acid pivaloyloxymethyl ester hydrochloride of melting point 169°-170° C. (dec.).

What is claimed is:

1. A process for producing a cephalosporin ester of the formula

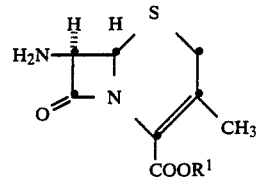

wherein $R^1$ is a group which is readily removable by hydrolysis, which process comprises reacting 7-amino-3-methyl-3-cephem-4-carboxylic acid in a partially chlorinated lower alkane selected from the group consisting of methylene chloride or chloroform with a bicyclic amidine of the formula

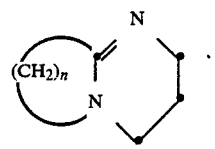

wherein n is the integer 3, 4 or 5, and a halide of the formula

   III wherein X is halogen and $R^1$ has the above significance, thereby producing compound Ia.

2. The process of claim 1, wherein methylene chloride or chloroform is used as the partially chlorinated lower alkane.

3. The process of claim 1, wherein 1,8-diazabicyclo[5.4.0]undec-7-ene is used as the bicyclic amidine of formula II.

4. The process of claim 1, wherein the bicyclic amidine is used in a slight deficiency.

5. The process of claim 1, wherein a pivaloyloxymethyl halide is used as the compound of formula III.

6. The process of claim 1, wherein a compound of formula III in which X is iodine is used.

7. The process of claim 1, wherein the reaction occurs at a temperature of about 0° C. to about 40° C.

8. A process for producing a cephalosporin ester of the formula

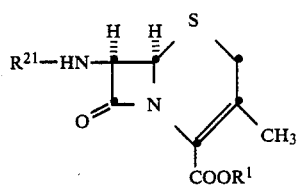

wherein $R^{21}$ is acyl and $R^1$ is group which is readily removable by hydrolysis, and of pharmaceutically acceptable acid addition salts of basic compounds of formula Ib which process comprises (a) reacting 7-amino-3-methyl-3-cephem-4-carboxylic acid in a partially chlorinated lower alkane selected from the group consisting of methylene chloride or chloroform with a bicyclic amidine of the formula

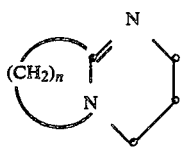
II wherein n is the integer 3, 4 or 5, and a halide of the formula

X—R¹   III wherein X is halogen and R¹ has the above significance, thereby forming a compound of the formula

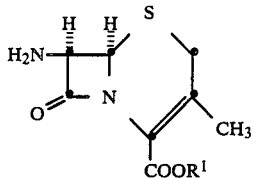
Ia wherein R¹ has the above significance, (b) treating the resulting compound of formula Ia with an unprotected or an optionally protected acylating agent; and (c) from the resulting compound cleaving off a protecting group which may be present thereby forming compound Ib.

9. The process of claim 8 further comprising treating a compound Ib so as to form a pharmaceutically acceptable acid addition salt thereof.

10. The process of claim 8, wherein the reaction steps are carried out in the same solvent and without isolating intermediates.

11. The process of claim 8, wherein 7-[2-(2-amino-4-thiazolyl)-2-(Z)-methoxyimino-acetamido]-3-methyl-3-cephem-4-carboxylic acid pivaloyloxymethyl ester or its hydrochloride is manufactured.

12. The process of claim 8, wherein 1,8-diazabicyclo[5.4.0]undec-7-ene is used as the bicyclic amidine of formula II; and a pivaloyloxymethyl halide is used as the compound of formula III.

13. The process of claim 12, wherein a compound of formula III in which X signifies iodine is used.

14. The process of claim 13, wherein 2-(2-amino-4-thiazolyl)-2-(Z)-methoxyimino-acetic acid 2-benzthiazolyl thioester is used as the acylating agent.

15. The process according to claim 14, wherein the reaction temperature in each step lies between about 0° C. and about 40° C.

* * * * *